United States Patent
Helmer

(10) Patent No.: US 9,517,312 B2
(45) Date of Patent: Dec. 13, 2016

(54) CAP ASSEMBLY FOR A DRUG DELIVERY DEVICE

(75) Inventor: Michael Helmer, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 168 days.

(21) Appl. No.: 13/877,856

(22) PCT Filed: Oct. 11, 2011

(86) PCT No.: PCT/EP2011/067685
§ 371 (c)(1),
(2), (4) Date: Apr. 4, 2013

(87) PCT Pub. No.: WO2012/049147
PCT Pub. Date: Apr. 19, 2012

(65) Prior Publication Data
US 2013/0211340 A1   Aug. 15, 2013

(30) Foreign Application Priority Data

Oct. 12, 2010  (EP) .................................. 10187270

(51) Int. Cl.
*A61M 5/32*   (2006.01)
(52) U.S. Cl.
CPC .......... *A61M 5/3276* (2013.01); *A61M 5/3205* (2013.01); *A61M 5/321* (2013.01); *A61M 5/3202* (2013.01)
(58) Field of Classification Search
CPC .. A61M 5/3202; A61M 5/3205; A61M 5/321; A61M 5/3276; A61M 5/3213; A61M 2005/3206; A61M 5/3245; A61M 5/3243; A61M 2005/3253; A61M 2005/3254; A61M 2005/3208

USPC ........................................................ 206/365
See application file for complete search history.

(56) References Cited

U.S. PATENT DOCUMENTS 5,941,857 A  *  8/1999  Nguyen ............... A61M 5/3205
                                                         604/195
8,882,706 B2 *  11/2014  Cronenberg ........ A61M 5/3202
                                                         604/110

FOREIGN PATENT DOCUMENTS

| CH | DE 102005061637 A1 * | 7/2007 | .......... A61M 5/3205 |
| DE | 102005061637 * | 7/2007 | .............. A61M 5/32 |
| DE | 102005061637 A1 | 7/2007 | |
| WO | 2005120611 A1 | 12/2005 | |
| WO | 2010072695 A1 | 7/2010 | |

OTHER PUBLICATIONS

Form PCT/IPEA/416, Notification of Transmittal of the International Preliminary Amendment on Patentability.

* cited by examiner

*Primary Examiner* — Nathan R Price
*Assistant Examiner* — Weng Lee
(74) *Attorney, Agent, or Firm* — McDonnell Boehnen Hulbert & Berghoff LLP

(57) ABSTRACT

The present invention relates to a cap assembly for a drug delivery device, comprising:
- a cap body (12) adapted to releasably engage with a housing of the drug delivery device and being further adapted to receive a needle assembly to be releasably interconnected with said housing,
- an ejector unit movably arranged on the cap body at least along the body's long axis and having mechanical transmission means adapted to transfer axial movement of the ejector unit to the needle assembly for ejecting the needle assembly from the cap body.

13 Claims, 5 Drawing Sheets

CAP ASSEMBLY FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2011/067685 filed Oct. 11, 2011, which claims priority to European Patent Application No. 10187270.3 filed Oct. 12, 2010. The entire disclosure contents of these applications are herewith incorporated by reference into the present application.

FIELD OF INVENTION

The present invention relates to a cap assembly for a drug delivery device, in particular for a pen-type injector, wherein the cap assembly is further designed as a tool for assembling and/or disassembling a removable needle assembly to a housing of the drug delivery device.

BACKGROUND

Drug delivery devices allowing for multiple dosing of a required dosage of a liquid medicinal product, such as liquid drugs, and further providing administration of the liquid to a patient, are as such well-known in the art. Generally, such devices have substantially the same purpose as that of an ordinary syringe.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose.

In order to meet these requirements, the number of parts and steps required to assemble the device and an overall number of material types the device is made from have to be kept to a minimum.

Typically, the medicinal product to be administered is provided in a cartridge that has a moveable piston or bung mechanically interacting with a piston rod of a drive mechanism of the drug delivery device. By applying thrust to the piston in distal direction, a certain amount of the medicinal fluid is expelled from the cartridge.

Drug delivery devices, such like pen-type injectors typically comprise a housing having a cartridge holder for receiving the cartridge filled with the medicinal product that has to be dispensed. The distal end section of a cartridge holder facing towards the patient during an injector procedure typically comprises a through opening that provides access to a sealed distal end of the cartridge. By way of said through opening, an injection needle or cannula may penetrate the elastic seal of the cartridge to establish a fluid interconnect allowing the medicinal product to be expelled from the cartridge.

Typically, the disposable injection needle is provided by way of a needle assembly for releasably fastening the injection needle to the cartridge holder. The needle assembly typically comprises a needle hub supporting the injection needle and having further a cupped receptacle with an inner thread to be screwed onto a correspondingly threaded distal socket of the cartridge holder. The needle hub is typically provided with a removable needle cap serving as a protection means for preventing inadvertent stitch damage.

For administering a dose of the medicament, the needle cap has to be removed, before the needle pierces the skin of the patient. Upon completion of the medicament injection procedure, the needle is removed from the biological tissue and prior to disassembling needle hub and cartridge holder, the protective needle cap should be mounted on the needle hub. Inadvertent stitch damages may particularly occur, when the patient mounts the needle cap back on the needle hub. This problem is getting even more severe when the patients are physically infirm and/or have impaired vision.

It is therefore an object of the present invention to provide an improved cap assembly for a drug delivery device that serves as a tool at least for disassembling a needle assembly from a cartridge holder of a drug delivery device. It is a further aim, to reduce the risk of stitch damages and to enhance patient safety. Moreover, the cap assembly should be easy in understanding by the patient of its use. The cap assembly should also be particularly cost efficient in terms of production costs and assembly expenditure.

SUMMARY

The cap assembly according to the present invention comprises a cap body which is adapted to releasably engage with a housing, in particular with a cartridge holder of a drug delivery device, such like a pen-type injector. The cap body not only serves as a protection means for the cartridge holder and the cartridge disposed therein. It is further adapted to receive a needle assembly which is to be releasably interconnected with the housing of the drug delivery device, in particular with its cartridge holder.

This way, the cap assembly provides a feature for assembling as well as disassembling needle assembly and cartridge holder.

The cap assembly further comprises an ejector unit moveably arranged on the cap body at least along the body's long axis and having mechanical transmission means that are adapted to transfer the longitudinal or axial movement of the ejector unit to the needle assembly for the purpose of ejecting and removing the needle assembly from the cap body. Since the cap assembly, and in particular its cap body is adapted to disassemble needle assembly and cartridge holder, the problem may arise, that the needle assembly is mechanically engaged and/or fastened to the cap body after its removal from the cartridge holder. By way of the ejector unit, cap body and needle assembly disposed therein can be easily separated from each other and the needle assembly can be separately discarded.

Since the cap assembly provides a tool for assembling and/or disassembling the needle assembly and the cartridge holder and further has an ejector unit for separating needle assembly and cap assembly, the patient no longer gets in direct contact with an unprotected needle, except when administering a dose.

In a preferred embodiment, the cap assembly, and in particular the cap body comprises a cupped receptacle for selectively receiving at least part of the housing, e.g. the cartridge holder, or body and/or for receiving at least part of the needle assembly in a proximal end section.

In the present context it is to be noted that during a dose injection procedure the distal direction faces towards the patient and the proximal direction of the cap assembly or drug delivery device, respectively faces away from a patient's area of application. Moreover, a longitudinal, hence axial movement of the ejector unit may comprise a longitudinal translational displacement as well as a rotational movement which, inevitably comprises an axial component of movement.

Typically, the cap body is of substantially cylindrical shape and is closed at its distal end section. Opposite, at is proximal end section, the cap body comprises a receptacle adapted to selectively receive the cartridge holder and/or the needle assembly, in particular for mutually assembling and/or disassembling needle assembly and cartridge holder. For this purpose, the needle assembly can be secured to the cap body such that a rotational and/or longitudinal displacement of the cap assembly relative to the housing of the drug delivery device transfers to a respective displacement of the needle assembly with respect to the cartridge holder.

In a further preferred embodiment, the ejector unit is slidably arranged on a proximal end section of the cap body. It is at least displaceable into an injection position in which the ejector unit at least partially protrudes from the proximal end section of the cap body. Typically, the ejector unit with a proximal end face protrudes in proximal direction from the edge of the receptacle of the cap body. Consequently, by displacing the ejector unit in distal direction with respect to the cap body, a respective proximally directed displacement can be transfer to the needle assembly fixed in the receptacle of the cap body. For this purpose, ejector unit and needle assembly mutually engage in such a way, that at least a proximal displacement of the ejector unit correspondingly transfers to a respective proximal displacement of the needle assembly with respect to the cap body.

The ejector unit is typically fastened to the cap body. It is slidably or even threadedly disposed thereon, such that either a longitudinal and/or rotational displacement of ejector unit relative to the cap body leads to a respective relative longitudinal ejecting displacement.

In a further embodiment, the ejector unit comprises at least one radially inwardly protruding pin guided in a longitudinal slot of the cap body. The slot preferably extends in axial direction but may also be skewed with respect to the long axis of the cap body. Preferably, the ejector unit at least partially surrounds the proximal end section of the cap body, wherein mutual displacement of ejector unit and cap body is governed by the course of the cap body's longitudinal slot adapted to guide the pin of the ejector unit. By said engagement of pin and longitudinal slot, the ejector unit positively engaged with the cap body is free to move with respect to the cap body within pre-defined margins that are determined by the elongation and/or course of the slot.

In another preferred aspect, the ejector unit comprises a substantially cylindrical sleeve surrounding the proximal end section of the cap body. The cylindrical sleeve of the ejector unit is typically adapted to the shape and geometry of the proximal end section of the cap body. Moreover, geometry and outer contour of the cap body may be designed and adapted to the shape and geometry of the ejector unit, such that cap body and ejector unit comprise an aesthetic design.

According to another embodiment, the cap body comprises an interlock means for rotatably interlocking the cap body and the needle assembly. Preferably, cap body and needle assembly comprise mutually corresponding interlock means for rotatably securing cap body and needle assembly. By way of a rotation interlock, the needle assembly can be screwed onto the cartridge holder as well as unscrewed therefrom by making use of the cap assembly.

In a further aspect, the cap body comprises at least one circumferential groove at its inner side wall, wherein said groove is adapted to receive at least one radially outwardly protruding stud of the needle assembly. Stud and groove can be mutually engaged, e.g. by way of a snap-in function providing a mutual fixing of needle assembly and cap body at least in longitudinal direction. By way of inter-engaging groove and stud, the cap body may freely rotate with respect to the needle assembly at least within a predefined margin defined by the circumferential elongation of the groove.

In a further preferred embodiment, the groove at the inner side wall of the cap body is universally adapted to selectively receive the at least one stud or a corresponding and radially protruding snap-fit means of the housing of the drug delivery device. The snap-fit means adapted to attach the cap assembly to a body of the housing of the drug delivery device is either disposed directly on said body or on a proximal section of the cartridge holder of the drug delivery device. This way, the circumferential groove provides at least two functions. It serves as a fastening means to secure the cap assembly to the housing of the drug delivery device and further serves as a means to transiently mount the needle assembly to the cap assembly for the purpose of mutually assembling needle assembly and cartridge holder of the drug delivery device.

In a further preferred embodiment, the groove of the cap body is disposed in direct vicinity of the open end of the cap body. Irrespective of its location inside the cap body, the groove comprises at least one stop element disposed therein which is adapted to lock a rotational movement of the cap body relative to the needle assembly in at least one direction. Preferably, the stop element is designed as a discontinuity in the groove preventing a mutual free rotation of cap body and needle assembly. However, when cap assembly and needle assembly are mutually engaged, and when the groove comprises two oppositely diametrically positioned stop elements, the cap body can be rotated with respect to the needle assembly at maximum about 180°. Depending on the number of stop elements equidistantly arranged in the groove the maximum angle of rotation is reduced by 360° divided by the number of stop elements. For instance, with three stop elements, the maximum angle equals 120°, with four stop elements, the respective angle reduces to substantially 90°.

As soon as stop element and radially outwardly protruding stud of the needle assembly mutually engage or abut, any further rotation of the cap body forces the needle assembly to rotate accordingly. By means of the groove featuring at least one stop element, a rather simple and efficient means for longitudinally and rotationally securing cap body and needle assembly with respect to each other is provided.

The snap-in assembly of cap body and needle assembly requires that the radially outwardly protruding stud of the needle assembly and the stop element of the corresponding groove are arranged in a circumferential offset with respect to each other which is likely the case, when the groove only comprises a few, e.g. one, two, three or four equidistantly arranged stop elements. In this way, cap body and needle assembly may positively engage simply by putting or urging the cap assembly on the needle assembly by a kind of a proximally directed push movement. As soon as cap body and needle assembly inter-engage by way of mutually corresponding snap-fit means, the cap body can be rotated with respect to the needle assembly until radially outwardly protruding stud of the needle assembly and stop element of the cap body's groove mutually abut.

Any further relative rotation of cap body and cartridge holder or housing of the drug delivery device leads to a respective rotational and disassembling motion of the needle assembly relative to the cartridge holder.

Due to the snap-fit engagement, the entire needle assembly will rest in the receptacle of the cap assembly when removed from the cartridge holder. By way of the ejector unit, the needle assembly can be separated from the cap assembly and its cap body and the cap assembly can be put back on the cartridge holder as a protective cap.

Furthermore and according to another preferred embodiment of the invention, the ejector unit comprises a radially inwardly protruding rim at its proximal end section. When a needle assembly is disposed in the receptacle of the cap assembly, the inwardly protruding rim is adapted to axially abut with a radially outwardly protruding flange portion of the needle assembly. By having axial or longitudinal abutment of ejector unit and needle assembly, the needle assembly can be displaced in longitudinal direction by displacing the ejector unit relative to the cap body accordingly.

The inwardly protruding rim of the ejector unit may also abut with a proximal end section of the cap body, in particular, when the ejector unit is in an initial, hence idle position.

Alternatively and depending on the geometry of the needle assembly the ejector unit may already provide an ejecting function even without having a radially inwardly protruding rim at its proximal end section. Given that the radially outwardly protruding flange portion of the needle assembly is sufficiently large, a respective axial abutment of the ejector unit's proximal end and the respective flange portion of the needle assembly may provide a comparable axial abutment sufficient to transfer proximally directed displacement of the ejector unit to the needle assembly.

In a further independent aspect, the invention also relates to a needle assembly for a drug delivery device that comprises a needle hub having a needle mounted thereon. The needle hub further comprises fastening means for releasably engaging with a housing of the drug delivery device, in particular with a distal portion of a cartridge holder. Typically, said fastening means comprise an inner thread corresponding with an outer thread provided as a distal socket portion of the cartridge holder. In this way, the needle hub can be fastened and attached to the cartridge holder by way of screwing. Alternatively, a snap-fit engagement of needle hub and cartridge holder is conceivable.

The needle assembly further comprises at least one needle cap releasably mounted on the needle hub and further comprising at least one radially protruding stud which is adapted to engage with a corresponding groove inside a cap body of a cap assembly to be releasably engaged with the housing, i.e. the body and/or the cartridge holder of the drug delivery device. By way of the mutual engagement of groove and stud a rotational and/or longitudinal mutual interlocking of needle cap and cap body can be attained. Hence, the radially protruding stud disposed on the needle cap is adapted to provide a rotational and/or longitudinal interlock of needle cap and cap body or cap assembly, respectively.

The needle cap preferably comprises at least two or a plurality of radially protruding studs being arranged equidistantly on the outer circumference of the needle cap. The needle cap is preferably designed as an outer needle cap providing a protective sheath for the needle, which may be supplied with an additional inner protection cap.

The needle cap of the needle assembly is intended to be mounted back on the needle hub after injection of a dose of the medicament. In preferred embodiments, the needle cap will be at least longitudinally secured to a cap assembly of the drug delivery device as described. A user then only has to handle the cap assembly for putting on the needle cap on the needle hub. After having disassembled the needle assembly from the cartridge holder by making use of the cap assembly engaged with the needle cap, the entire needle assembly can be ejected from the cap assembly by making use of the ejector unit.

Therefore, the at least one needle cap preferably also comprises a radially outwardly protruding flange at a proximal end section that abuts with a proximal end section of the ejector unit.

In another preferred aspect, the invention also relates to a needle removing system for a drug delivery device that comprises a cap assembly as described above and a needle assembly. Here, the needle assembly comprises a needle hub having a needle mounted thereon and having further at least one needle cap releasably mounted on the needle hub. The needle cap and the cap assembly comprise mutually corresponding rotation locking means for rotatably interlocking the needle cap and the cap assembly. In this way, the cap assembly can be used as a tool for screwing or unscrewing the needle assembly to or from the cartridge holder.

In a preferred embodiment, the rotation locking means of the needle cap comprises a radially extending stud adapted to engage with at least one stop element disposed in a circumferential groove of the cap assembly, in particular of the cap body. Said groove is preferably disposed at an inner circumferential side wall of a cap body having a substantially cylindrical shape.

In another independent aspect, the invention also relates to a drug delivery device for dispensing of a medicament by way of injection. The device comprises a housing which is adapted to releasably engage with a needle assembly and further has a cartridge containing the medicament and being disposed in the housing. The drug delivery device, which preferably comprises a pen-type injector further comprises a cap assembly as described above.

Moreover and in another independent aspect, the invention also relates to a method of disengaging a needle assembly and a housing of a drug delivery device, wherein in a first step the needle assembly being mounted on a distal housing section of the drug delivery device is inserted into a cupped body of a cap assembly having a corresponding needle cap secured therein. By way of inserting the needle assembly into the cap assembly, on the one hand the needle cap secured in the cap assembly is mounted back on the needle assembly, thereby receiving the tipped needle of the needle assembly. On the other hand, by way of inserting the needle assembly into the cap body and into the needle cap, a positive engagement of cap assembly and needle assembly is attained, thus allowing to make use of the cap assembly as a tool for disassembling needle assembly and cartridge holder.

Hence, needle assembly and housing section can be mutually disengaged by translationally and/or rotationally displacing the cap assembly and the housing away from each other, such that the needle assembly is or remains secured to the cap assembly. After having disassembled needle assembly and cartridge holder, the needle assembly is secured in the receptacle of the cupped cap body. Then, by finally making use of an ejector unit being moveably arranged on the cap body in a longitudinal direction, the cap assembly can be displaced towards the open end of the cupped body for ejecting and disassembling the needle assembly from the cupped body, hence from the cap assembly.

Similarly, the needle assembly can also be mounted on the cartridge holder by making use of the cap assembly, e.g. by inserting a needle assembly into the hollow cap and by making use of the cap body as a tool for screwing the needle assembly onto the cartridge holder. Applying a force to the cap assembly in distal direction relative to the body of the housing of the drug delivery device, then leads to a disassembly of needle cap and needle hub, wherein the needle cap remains fastened to the cap assembly.

The drug delivery device can then be used for injecting a medicament before the needle cap is re-mounted to the needle hub by way of the cap assembly. Preferably, the cap is designed such that multiple use of a needle assembly is not possible.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be explained in greater detail by making reference to the drawings in which:

FIG. 6 shows a perspective illustration of a needle assembly secured in a cap assembly and . . .

DETAILED DESCRIPTION

Figure 1:
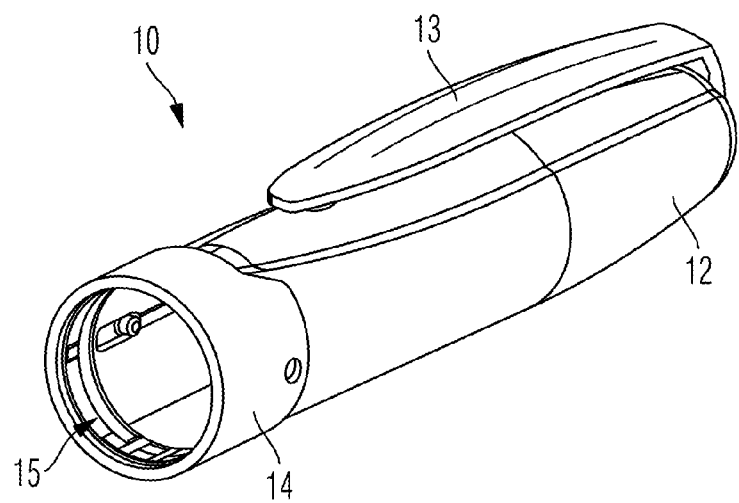
FIG. 1 shows a cap assembly according to the present invention in a perspective illustration.
Figure 6:
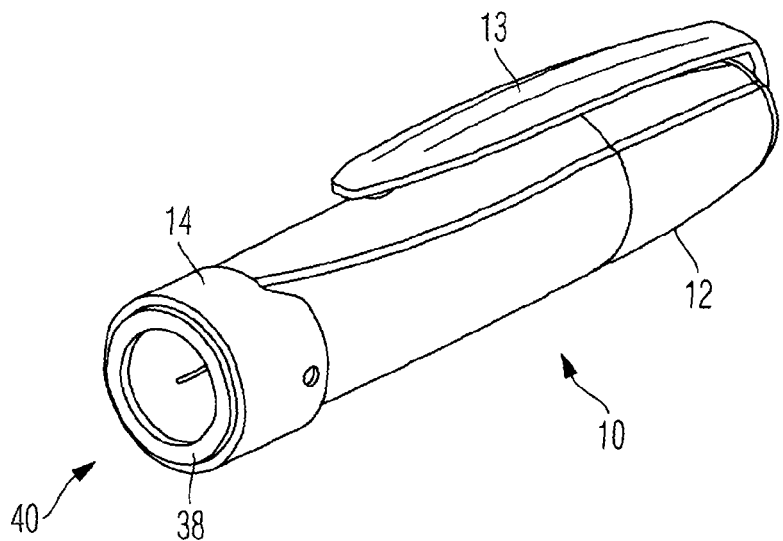
Figure 7:
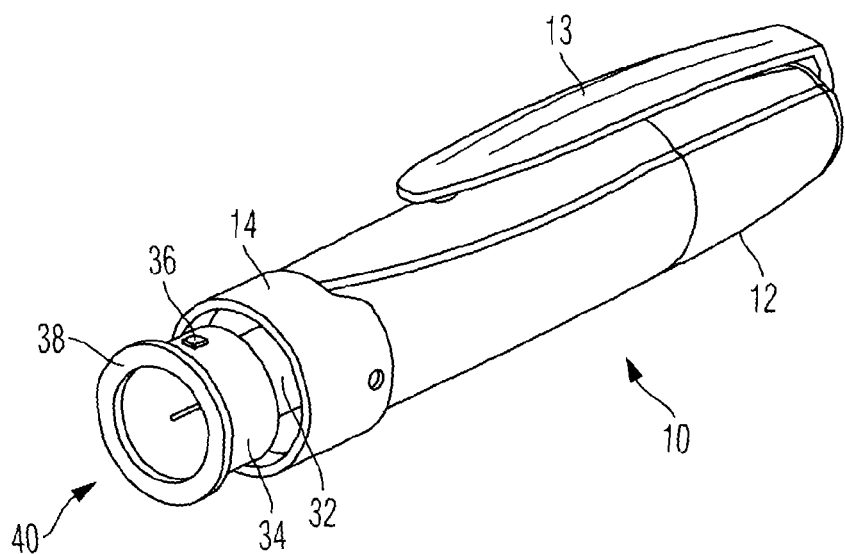
FIG. 7 shows needle assembly and cap assembly according to FIG. 6 with an ejected needle assembly.

In the perspective illustrations of FIGS. 1, 6 and 7, a cap assembly 10 of a drug delivery device and in particular of a pen-type injector is separately illustrated. The cap assembly 10 comprises a substantially cylindrical cap body 12 comprising a cupped receptacle 15. Additionally, the cap assembly comprises a clip 13 for fastening the cap 10 and/or the entire drug delivery device for instance to a piece of cloth.

The cap assembly 10 originally serves as a protection means for a cartridge holder 46 of a drug delivery device, which is not further illustrated here. The cap body 12 as further illustrated in FIGS. 2, 3 and 4 therefore comprises an annular or circumferential groove 20 at an inner side wall close to its proximal end. By way of said groove 20, the cap body 12 can be releasably attached to either a cartridge holder 46 or to a body or other, not explicitly illustrated housing components of the drug delivery device.

Figure 2:
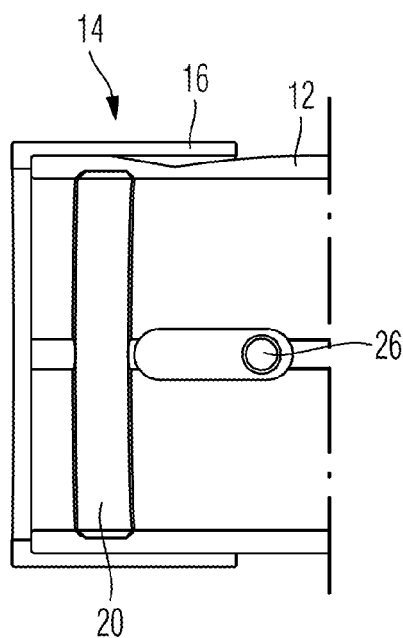
FIG. 2 shows a proximal end of the cap assembly according to FIG. 1 in an enlarged view with the ejector unit in an initial position.
Figure 3:
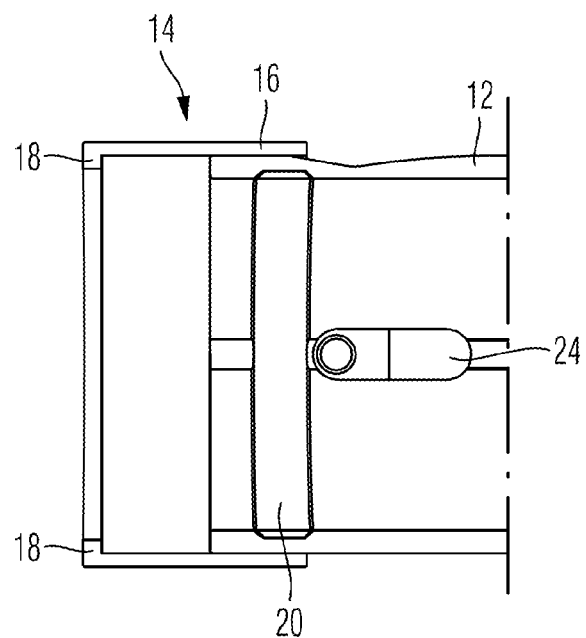
FIG. 3 shows the cap assembly according to FIG. 2 with its ejector unit in ejecting position.
Figure 4:
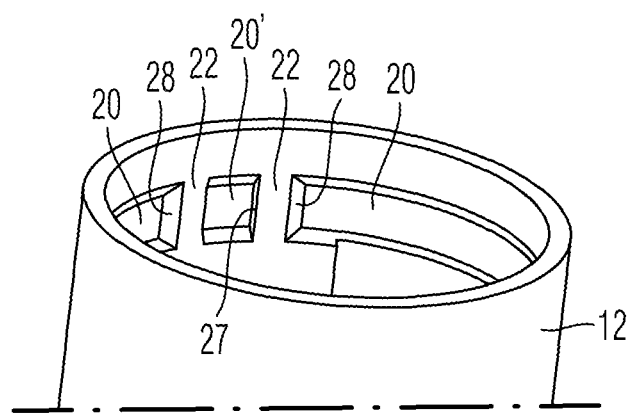
FIG. 4 illustrates the proximal end of the cap body, FIG. 5 schematically shows a outer needle cap.

The cap assembly 10 further comprises an ejector unit 14 having a cylindrical sleeve 16 which is mounted at the outer circumference of the proximal end of the cap body 12. At its proximal end, and as illustrated in FIG. 3, the ejector unit 14 comprises a radially inwardly protruding flange 18, which in initial configuration of the ejector unit as shown in FIG. 2 abuts with a proximal end of the cap body 12. Additionally, the ejecting sleeve 16 and the cap body 12 are secured and positively engaged to each other by way of a pin 26 pointing radially inwardly from the inner side wall of the ejector sleeve 16. Said pin 26 is guided in a longitudinal slot 24 of the cap body 12.

This way, the ejector unit 14 is slidably supported on the outer circumference of the proximal end of the cap body 12. The annular groove 20 of the cap body is further illustrated in FIG. 4 in detail. As shown in the perspective illustration, the groove 20 is interrupted by two stop elements 22 forming a receptacle 20' there between. The stop elements 22 integrally formed with the cap body comprise bevelled side sections 28 facing away from each other and further comprise rather steep, substantially radially extending side sections 27 facing towards each other. The annular groove 20 is not only adapted to receive a corresponding snap-fit element or radial protrusion of the cartridge holder 46 or of the body of the drug delivery device but is also intended to receive radially extending studs 36 disposed on the outer circumference of an outer needle cap 30 of a needle assembly 40 as shown in FIGS. 5 through 7.

Figure 9:
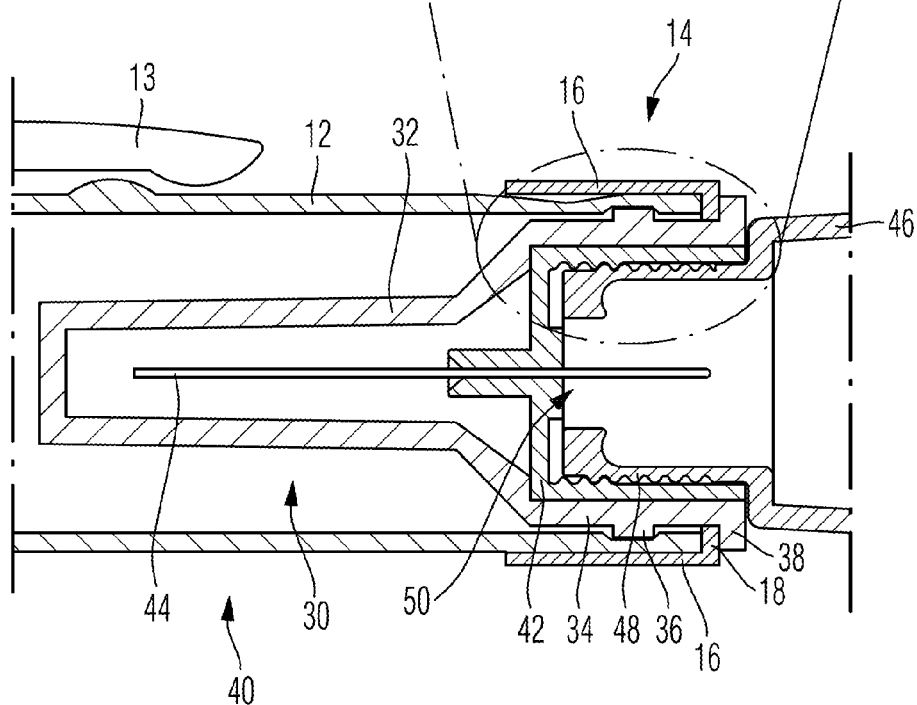
FIG. 9 shows a longitudinal cross section of needle assembly and cap assembly mounted on a cartridge holder section in an initial configuration and FIG. 10 shows the assembly according to FIG. 9 with the ejector unit in ejecting position.
Figure 10:
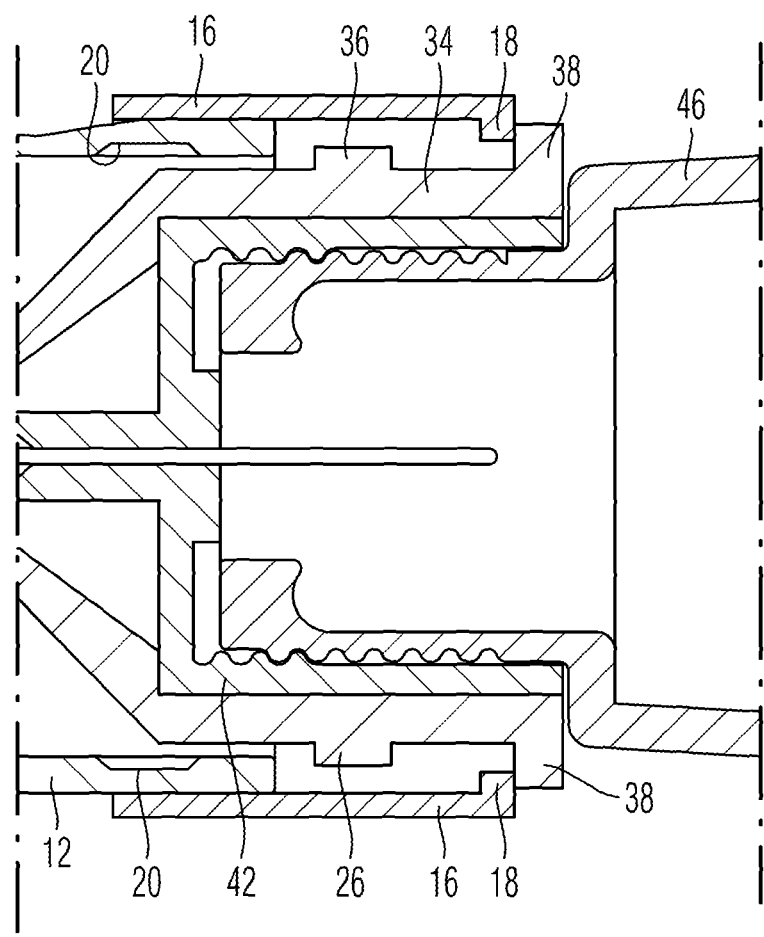

The needle assembly 40 as entirely illustrated in cross section in FIG. 9, comprises a needle hub 42 to be threadedly engaged with a distal support section 48 of a cartridge holder 46. The needle hub 42 supports the needle 44, which in assembly configuration as illustrated in FIG. 9 reaches through a through opening 50 arranged in a front or distal surface the cartridge holder 46. The needle assembly 40 further comprises an outer needle cap 30 to be positively and/or frictionally but releasably engaged with the needle hub 42.

Figure 5:
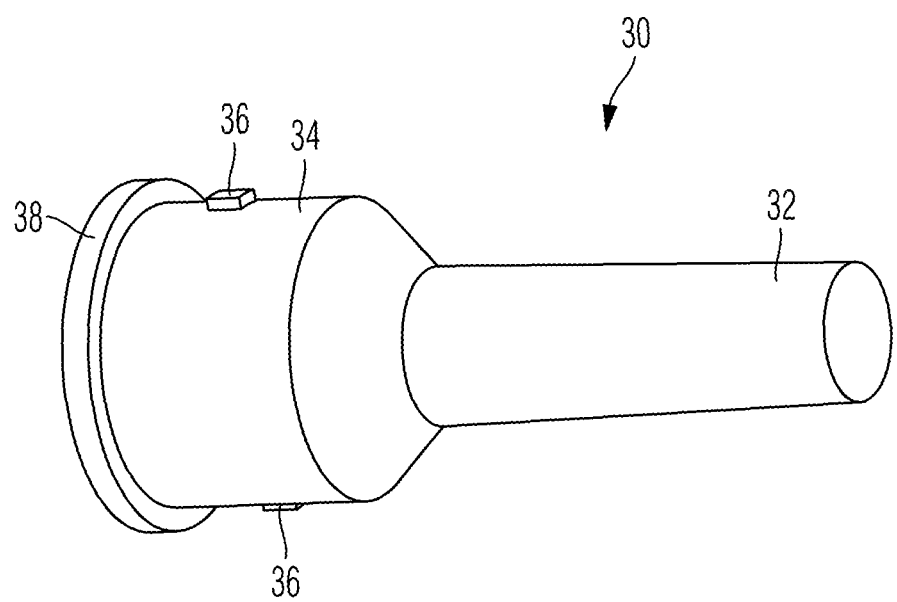

The outer needle cap 30 as illustrated in FIG. 5 comprises a sheath section 32 adapted to receive the needle 44, which in turn may be separately protected by a inner needle cap not further illustrated here. The outer needle cap 30 further comprises a socket portion 34 adapted to receive the needle hub 42. The socket portion 34 of substantially cylindrical geometry comprises the radially protruding and diametrically oppositely arranged studs 36. The proximal end of the socket 34 is provided with an annular rim 38 radially protruding from the socket portion 34.

Figure 8:
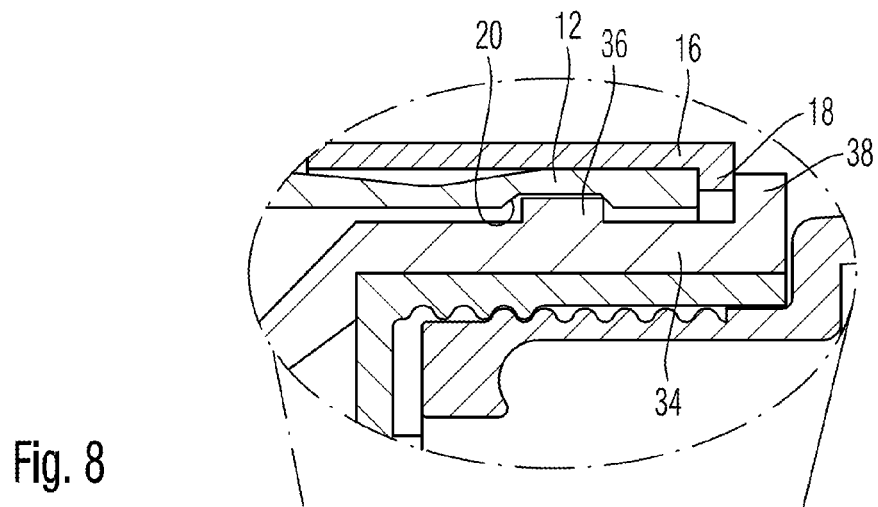
FIG. 8 shows an enlarged view of the interface of cartridge holder, needle assembly, cap assembly and ejector unit as shown in FIG. 9.

As further illustrated in FIGS. 8 and 9, the outer needle cap 30 is adapted to positively engage with the cap body 12. Hence, the entire needle assembly can be inserted into the receptacle 15 of the hollow pen cap assembly 10 until the studs 36 mate with the inner annular groove 20 of the cap body 12. This way, at least a positive engagement of needle cap 30 and cap assembly 10 can be attained. When the cap assembly 10 or its cap body 12 is then rotated with respect to the needle assembly 40, which in turn may be screwed and fastened to the cartridge holder 46, the studs 36 of the outer needle cap 30 will be guided along the groove 20 until they reach a corresponding stop element 22.

Depending on their corresponding shape and geometry, the stop element 22 itself may but against the radially protruding stud 36, thus providing an at least uni-directional rotational interlock of cap body 12 and outer needle cap 30. In the embodiment according to FIG. 4, wherein the stop element 22 comprises a bevelled or slanted side sections 28 towards the adjacently extending groove 20, the cap body 12 and the needle cap 30 may be rotated with respect to each other until the studs 36 snap into the groove portion 20', comprising an annular extension corresponding to the annular extension of the stud 36. In this way, a bi-directional rotational lock of cap body 12 and outer needle cap 30 can be attained.

As further illustrated in FIGS. 8 and 9, the radially protruding annular rim 38 of the needle cap 30 buts against the radially inwardly directed flange portion 18 of the ejector unit 14. By way of displacing, in particular sliding the ejector sleeve 16 in proximal direction, i.e. towards the cartridge holder 46, the snap-fit engagement of stud 36 and groove 20 can be released an the needle assembly 40 as a whole can be ejected from the pen cap assembly 10, as for instance indicated in FIG. 7.

Assembling and disassembling of a needle assembly to a cartridge holder 46 of a drug delivery device is as follows. A new needle assembly can either be manually screwed onto a cartridge holder 46 or can be alternatively clipped into the cap body 12 of the pen cap assembly 10 as illustrated for instance in FIG. 6. When inserted into the cap body 12, the pen cap assembly 10 can be used as a tool to screw the needle assembly 40 and in particular its needle hub 42 onto the correspondingly threaded distal section 48 of the cartridge holder 46. Typically, prior to mounting the needle assembly onto the cartridge holder a respective protection foil is removed from the needle assembly Typically, when clipping or inserting the outer needle cap 30 into the cap body 12 in an arbitrary angular position, the studs 36 of the outer needle cap 30 typically mate with the groove 20. In the course of screwing the needle hub 42 onto the threaded distal support 48 of the cartridge holder 46, the studs 36 of the outer needle cap 30 will be locked in the groove section 20'. When a final assembly position of the needle assembly 40 on the cartridge holder 46 is attained, as illustrated in FIG. 9, the pen cap assembly 10 can be removed from the cartridge holder 46, wherein the outer needle cap 30 remains fastened in the cap body 12, thus setting free the needle 44.

The drug delivery device is then ready to set and to dispense a dose of the medicament contained in the cartridge, which is placed inside the cartridge holder 46 and which is in fluid communication with the injection needle 44. Typically, the needle itself is further protected by way of an inner disposable needle cap. This has to be removed prior to injection.

After the injection procedure, the cap body 12 together with the outer needle cap 30 secured therein can be put back onto the needle hub. Since outer needle cap 30 and needle hub 42 mutually engage by way of a force or clamping fit, a torque externally applied to the cap body 12 relative to the cartridge holder 46 then leads to an unscrewing of the needle hub 42. When the threaded engagement of needle hub 42 and support section 48 of the cartridge holder 46 is released, the cap body 12 can be removed from the cartridge holder 46. The needle assembly 40 is then fastened to the pen cap assembly 10 as illustrated in FIG. 6. Then, by displacing the ejector unit 14 in proximal direction, the flange portion 18 of the ejector sleeve 16 transfers a respective proximally directed force and hence a corresponding motion to the outer needle cap 30 via its annular rim 38.

This way, snap-fit interlock of cap body 12 and outer needle cap 30, and hence needle assembly 40 can be effectively released, leading to an ejecting of the needle assembly 40 as illustrated in FIG. 7.

The invention claimed is:

1. A cap assembly for a drug delivery device, comprising:
   a cap body adapted to receive a needle assembly to be releasably interconnected with a housing of the drug delivery device, and
   an ejector unit movably arranged on the cap body at least along the body's long axis and comprising a mechanical transmission means adapted to transfer at least an axial displacement of the ejector unit to the needle assembly for ejecting the needle assembly from the cap body,
   wherein the ejector unit is slidably arranged on an outer circumference of a proximal end section of the cap body,
   wherein the ejector unit is at least displaceable into an ejecting position to eject the needle assembly from the cap body, wherein, in the ejecting position, the ejector unit at least partially protrudes in a proximal direction beyond a proximal end of the cap body,
   wherein the cap body comprises an annular groove at an inside facing portion of its sidewall to releasably engage with the housing of the drug delivery device, and
   wherein the cap body comprises a cupped receptacle for selectively receiving at least a portion of a cartridge holder or body of the drug delivery device.

2. The cap assembly according to claim 1, wherein the cupped receptacle is adapted to selectively receive at least part of the housing and/or at least part of the needle assembly in the proximal end section.

3. The cap assembly according to claim 1, wherein the ejector unit comprises at least one radially inwardly protruding pin guided in a longitudinal slot of the cap body.

4. The cap assembly according to claim 1, wherein the ejector unit comprises a substantially cylindrical sleeve surrounding the proximal end section of the cap body.

5. The cap assembly according to claim 1, wherein the cap body comprises an interlock means for rotatably interlocking the cap body and the needle assembly.

6. The cap assembly according to claim 1, wherein the annular groove is adapted to receive at least one radially outwardly protruding stud of the needle assembly.

7. The cap assembly according to claim 6, wherein the annular groove is adapted to selectively receive the at least one stud or a snap-fit means of the housing.

8. The cap assembly according to claim 6, wherein the annular groove comprises at least one stop element disposed in the annular groove and being adapted to lock a rotational movement of the cap body relative to the needle assembly in at least one direction.

9. The cap assembly according to claim 1, wherein the mechanical transmission means of the ejector unit comprises a radially inwardly protruding rim at its proximal end section adapted to axially abut with a radially outwardly protruding flange portion of the needle assembly and/or with the proximal end section of the cap body.

10. A needle removing system for a drug delivery device comprising:
   a cap assembly according to claim 1,
   a needle assembly comprising a needle hub and at least one needle cap releasably mounted thereon, wherein the needle cap and the cap assembly comprise mutually corresponding rotation locking means for rotatably interlocking the needle cap and the cap assembly.

11. The needle removing system according to claim 10, wherein the rotation locking means of the needle cap comprises a radially extending stud adapted to engage with at least one stop element disposed in the annular groove of the cap assembly.

12. A drug delivery device for dispensing of a medicament by way of injection, comprising:
   a housing, adapted to releasably engage with a needle assembly,
   a cartridge containing the medicament and being disposed in the housing, and
   a cap assembly according to claim 1.

13. A method of disengaging a needle assembly and a housing of a drug delivery device comprising the steps of:
   inserting the needle assembly mounted on a distal housing section of the drug delivery device into a cupped body of a cap assembly having a corresponding needle cap secured therein,
   mutually disengaging the needle assembly and the housing section by translationally and/or rotatably displacing the cap assembly and the housing away from each other, wherein the needle assembly is secured to the cap assembly, and
   displacing an ejector unit slidably arranged on an outer circumference of a proximal end section of the cap body in a longitudinal direction towards the open end of the cupped body and into an ejecting position to eject the needle assembly from the cap body,
   wherein, in the ejecting position, the ejector unit at least partially protrudes in a proximal direction beyond a proximal end of the cap body for ejecting the needle assembly from the cap assembly, and
   wherein the cap body comprises an annular groove at an inside facing portion of its sidewall to releasably engage with the housing of the drug delivery device.

* * * * *